Figure 1:
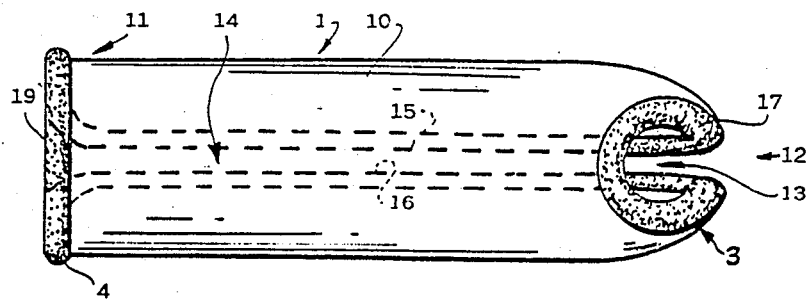

United States Patent [19]

Immonen

[11] Patent Number: 4,893,616
[45] Date of Patent: Jan. 16, 1990

[54] IMPOTENCE SUPPORT

[76] Inventor: Toivo Immonen, Vellamonkatu 16 A 1, SF-00550 Helsinki, Finland

[21] Appl. No.: 148,857

[22] Filed: Jan. 27, 1988

[30] Foreign Application Priority Data

Jul. 17, 1987 [DE] Fed. Rep. of Germany ....... 3723746

[51] Int. Cl.$^4$ .............................................. A61F 5/41
[52] U.S. Cl. .................................................... 128/79
[58] Field of Search ......................................... 128/79

[56] References Cited

U.S. PATENT DOCUMENTS

| | | | |
|---|---|---|---|
| 844,798 | 2/1907 | Hawley | 128/79 |
| 1,362,398 | 12/1920 | Crawford et al. | 128/79 |
| 2,868,192 | 1/1959 | Dannen | 128/79 |
| 3,939,827 | 2/1976 | Brunstetter | 128/79 |
| 4,615,337 | 10/1986 | Allinson | 128/79 |

Primary Examiner—John J. Wilson
Assistant Examiner—Cary E. Stone
Attorney, Agent, or Firm—Webb, Burden, Ziesenheim & Webb

[57] ABSTRACT

The invention is an impotence support, horizontally split, made of plastics, to be fitted over the penis (2), for the performance of sexual intercourse with a shortened and slackened penis. The end portion (3) of the impotence support is rounded and tapers anatomically to fit and correspond to the deeper portion of the neck groove of the penis glans (22) with the longitudinal split (14) so located that the frenum (26) of the glans remains free. This ensures that the glans is kept free and makes possible extension of the penis and the retention of this state of extension during intercourse. The support end edges (15,16) lie hidden behind the glans (22) and the support does not protrude outside the ridge of the glans (22). Retention of the support in place can be ensured with a binding which extends over the longitudinal split (14).

10 Claims, 1 Drawing Sheet

IMPOTENCE SUPPORT

The present invention relates to a device for assisting those suffering from impotence.

A great many men, especially the elderly, suffer lack of rigidity in the penis, which problem concerns their partners. In addition, many men attain orgasm before their partner which can leaves their partner unsatisfied. It also causes depression and ruins sexual relationships.

Because of the seriousness of the problem many solutions to the problem have been proposed which basically can be divided into internal and external supports for the penis.

For external support a supporting sleeve is fitted around the penis, examples of which are: U.S. Pat. No. 2,868,192 conically narrowing tube, which is threaded over the penis for its support; U.S. Pat. No. 3,393,827 and DE Pat. No. 875853 constructed to go over part of the penis behind its glans, retention of the support in place being with the aid of adhesive tape; split tubes similar to DE utility models 7243079 and 6934602 to be spread and pressed clipwise around the part of the penis behind the glans; and split tubes similar to DE Pat. No. 3100491 that are fitted over the extended part of the penis, and the retention in place of which it is tried to ensure by turning the foreskin over the support and fastening it with adhesive film to the outer surface of the support.

To enable a person suffering from impotence to have sexual intercourse and also bring satisfaction to his partner the support bo be used should fulfil at least the following requirements:
   the head of the penis must be free and remain free during intercourse, to allow good contact and excitation in intercourse,
   the urethrea of the penis must not be subjected to compression so that normal ejaculation of semen is not prevented,
   the support should not irritate or damage the penis, nor the vagina
   with the aid of the support it must be possible to attain full growth of a short, slack penis.

The previously known supports all rely on the basic assumption that it is sufficient if a slack penis is given support. From the intercourse aspect it is also essential that the penile dimensions can grow to be at least close to the dimensions of the normally erect penis. The solution to that problem cannot be obtained with the previously known supports and additionally in several of the previously known supports the following significant disadvantages are present.

In the solution disclosed in U.S. Pat. No. 2,868,192 the support tube has no split and therefore is threaded over the penis with difficulty. In addition, as it is drawn over the penis the mouth of the tube is so flexible that no unformed mouth opening can possibly stay behind the glans and the support tube just slides over the glans. Extension of the penis with the tube in question is not successful.

In the supports of U.S. Pat. No. 3,939,287 and DE 875853 the mouth of the support is not reduced to the dimensions of the glans neck groove and in addition sharp rims are formed immediately behind the glans, so that the penis cannot be extended sufficiently in intercourse and the glans slips through the mouth opening into the support during intercourse. Furthermore the edges of the wide mouth rub the vagina and go over the penis frenum, as the result of which the frenum is squeezed and may even tear.

In solutions according to utility models nos. 6948467 and 7243079 the penis support at the glans end is completely unformed and unrestricted, so that the support slides over the glans and abrades the vagina. Nor is extension of the penis successful with the support in question.

The support according to publication DE3100491 is only suitable for persons possessing a long foreskin as the retention of the support in its place is ensured by fastening the foreskin drawn over the support to the support surface with a binding, which irritates. In addition the split and in particular the mouth opening edges are not rounded off so that a rather painful local irritation is set up on the foreskin. Extension of the penis is not successful with the support in question.

Because previously known external supports have not achieved the desired result attempts have also been made to find solutions for impotency problems by means of so-called internal penile supports. A permanent prosthesis is internally set in the penis by surgical procedures, the principal objective of which is a sufficient extent of penile rigidity for intercourse. Disadvantages of the solution are however the expense and the permanence, which in itself makes normal life difficult.

The objective of the invention is to provide an improved impotence support particularly for the care of impotency problems and also to make possible the continued act of intercourse.

Accordingly, the present invention provides a support for a penis comprising an open ended tubular element one end of which is shaped to taper down anatomically to fit into the deeper portion of the glans neck groove while leaving the penis frenum free, and preventing the foreskin moving forward during intercourse.

Thus the invention is founded on the ingenious basic perception that the end part of the impotence support is rounded off and made to taper down anatomically to fit and correspond with the deepening of the glans neck groove whilst the penis frenum can be left free. Due to this kind of end part shape the end edges of the support remain hidden behind the glans and the support does not protrude outside the glans ridge. The support according to the invention both stays firmly behind the glans, thus enabling extension of the penis, and reliably prevents the foreskin pushing forward during intercourse.

The present invention is further described hereinafter by way of example, with reference to the accompanying drawings, in which:

FIG. 1 presents an impotence support according to the invention as seen from above.

Figure 2:
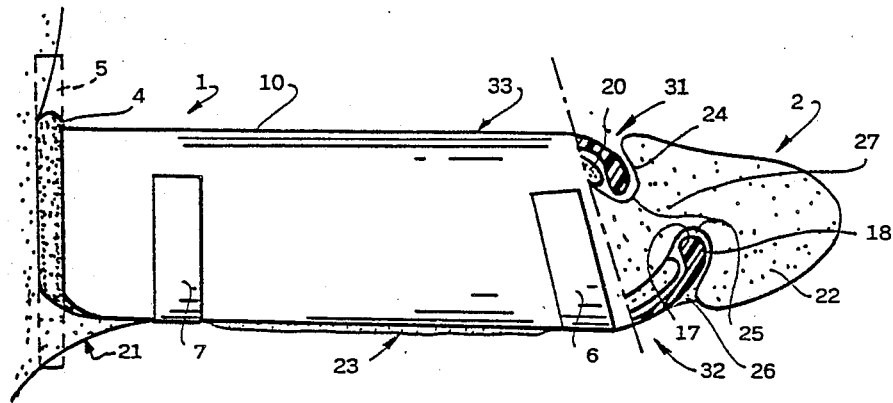
Figure 3:
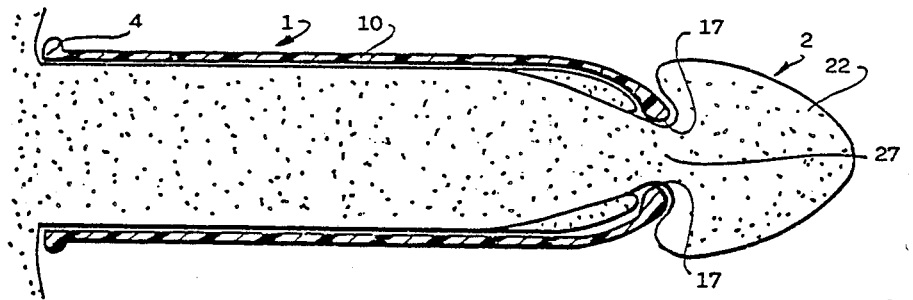
Figure 4:
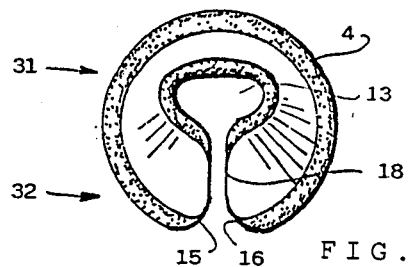

FIG. 2 presents a partial cross-sectional side view of the impotence support according to the invention, which is fitted onto the penis;

FIG. 3 presents a cross-sectional view of the impotence support according to the invention, as seen from above; and FIG. 4 presents the impotence support according to the invention as seen directly from the front, that is from the glans end.

The first advantageous mode of application of the invention according to FIG. 1 most advantageously consists of a tubelike shell element 1, 8–13 cm long, at least in part elastic, advantageously made of plastic-based material, in which in element wall 10 is the longitudinal split 14. In the shell element 1 is the first open end 11, meant to be directed towards the penis root and the other open end 12 meant to be directed towards the penis tip, end 12 being tapered and rounded off and in which is the impotence support mouth opening 13. For the rounding off and softening of all edges according to the invention, particularly those of the mouth opening 13 and split 14, to be individually suitable, a suitable adhesive or softening material an be used e.g. Bostik 1782 adhesive or denture softening material.

As can be seen from FIGS. 2 and 3 the impotence support according to the invention is fitted over the extended penis 2 and its part 23, which is between the penis root 21 and glans 22, whilst the foreskin 20 is drawn back. In order to enable fitting on of the impotence support there is, as already stated above, a longitudinal split 14 in the shell element 1, when the impotence support is fitted by gripping its edges 15 and 16 and spreading its around the projecting part 23 of the penis 2 up to the glans 22.

In order that the opposing edges 15 and 16 limiting split 14 of shell element 1 do not cause squeezing or chafing to penis 2 nor abrade the mucous membranes of the vagina, they are rounded off and dimensioned to fit onto the penis 2 at a distance from each other further advantageous that there is a radially elastic liplike reinforcement to the edges 15 and 16 of split 14, the purpose of which is on one hand to increase the comfortability of use of the importance support according to the invention and on the other hand to stiffen the impotence support against longitudinal collapse, when the impotence support is fitted during intercourse round the aforementioned part 23 of penis 2 in the longitudinal direction is essentially uncollapsible and keeps the penis 2 extended to its full dimensions and supports it.

The split 14 according to the advantageous mode of application of the invention is positioned to run in the direction of the shell element 1 plane of symmetry from the underside of shell element 1 from the one end 11 to the other end 12, the frenum of the penis then being left completely free and no abrasive irritation occurs there.

At the other end of the shell element 1 in the advantageous mode of application according to the invention at the glans 22 end is the end part 3, which is shaped to reduce towards glans 22. It then has the upper half 31, curving towards the glans 22 and the lower half 32, curving towards the glans 22, of which the height of the upper half is greater in the vertical plane in the direction of the plane of symmetry than the height of the lower half.

In the upper half 31 is located a mouth part 13, intended to be positioned according to glans 22 and fitted around the neck groove 27 in question, the size of which mouth part, i.e. the diameter is to advantage between 1.0 ... 1.8 cm, most advantageously about 1.3 cm. The limiting wall surface 33 in the upper end piece half is anatomically formed to correspond with and give support to the sloping rear surface 24 of the glans 22. In addition the edge 17 of the wall 10 limiting the mouth part 13 of the shell element 1 is shaped and dimensioned to suit the deepening of the neck groove 25 of the glans 22.

The lower half 32 is divided into two by the aforementioned split and there are located the outermost tip (or tips) 18. The edges 15 and 16 of the split 14 in this lower half are so formed that on the impotence support being fitted onto the penis behind the glans the frenum 26 is left free whereupon the tips 18 come against the deepening 25 of the glans 22 neck groove and the edges 15, 16 of the split 14 on the penis 2 following the frenum 22 on both sides.

Because the mouth part 13 of the end part 3 of the impotence support according to the invention and all the edges 15, 16, 17 of the support 1 concerned with end part 3 remain behind the ridge of the glans 22 the support according to the invention does not abrade the mucous membranes of the vagina. Further because the end part tightly and accurately supports the deepening 25 of the glans neck groove with its aid the penis 2 an be extended and also the glans can be reliably prevented not only from drawing back inside the support but it also prevents the foreskin 20 from sliding in between the edge 17 of mouth opening 13 and the neck groove 25 and further from between the support and glans 22 to the end of glans 22.

In order that the impotence support according to the invention besides providing rigidity should also, to a sufficient extent, come against the body, it is advantageous that in the support first end on the body side there is a strengthened zone. If an advantageous mode of application of the impotence support according to the invention, this is carried out with a liplike strengthening, which is applied at edge 19 limiting the first open end 11. It is then most advantageous that there is combined liplike thickening 4 at all edges of shell element 1. Alternatively instead of the liplike thickening to the first open end or in addition to this a suitable flangelike thickening 5 can be used, which in FIG. 2 is denoted by a broken line.

As is most clearly indicated from FIG. 2 in the impotence support according to an advantageous mode of application of the invention there is a binding element 6 extending bridgewise over split 14, advantageously an adhesive plaster or corresponding tape element, which is fastened to the outer surface 33 of wall 10 of shell element 1, for the restriction and compression of the mouth part 13 of shell element 1 firmly into the neck groove 25 of glans 27 to stay the size of glans neck 27 during intercourse. In the fastening of the binding element 6 it must be taken into account that there is good cause to locate the binding element the closer to mouth part 13 the softer the impotence support used, in order that it can be ensured that the end part 3 remains behind the glans 2. The commercially obtainable "Micropore" plasters can be used with most advantage as binding element 6.

As further appears from FIG. 2 in the advantageous mode of application of this invention the retention of the impotence support first end 11 side end and the central part around penis 2 is ensured with a second binding 7, advantageously plaster or corresponding tape, which is extended bridgewise over split 14 and fastened to the outer surface 33 of wall 10 of shell element 1. Naturally several of these other binding elements can be used. The commercially available "Micropore" plasters can be used to advantage.

The impotence support according to the invention is presented in FIG. 4 directly from the front in order to demonstrate the characteristic specific to its invention, that the diameter of the mouth piece is fundamentally smaller than the diameter of the shell element in other parts.

In this connection, there is reason to conclude that an impotence support according to the invention can also be manufactured of a material that will, after spreading and fitting around the penis, recover its shape to some extend and squeeze clipwise the part 23 between the penis root and the glans 22. For the retention of bindings 6, 7 in place and also for prevention of them and also the edges of split 14 possibly having an irritational effect on the vagina, it may be necessary to draw a condom over the impotence support, when for the achievement of immediate contact it is advantageous to cut away the tip of the condom and set the cut edge to the neck of the glans.

Excitation nodules can be made on the surface of the impotence support for a partner slow in excitation and thickening for the looser than normal vagina, either at the manufacturing stage or on the initiative of the user.

The invention has only been described in the foregoing with the aid of some of its advantageous modes of application. It has naturally not been desired to limit the invention only to concern such individual modes of application and as will be clear to the professional person in the field many versions and variations are possible within the bounds of the attached patent requirements. Because of anatomical differences the user can make variations in form, especially to the end part, the mouth opening of shell size, cutting can then be used and/or commercially available adhesive materials e.g. BOSTIK 1782, as well as for the softening of edges and support surface denture softeners or some similar substance.

I claim:

1. A penis support for enabling sexual intercourse to be performed by a sufferer of impotency, comprising a tubular shell element having a first open end for facing the root of the penis and a second open end for facing the top of the penis, and a longitudinal split extending down said tubular shell element from said first open end to said second open end; wherein said second open end is formed with a mouth portion adapted to fit behind the penis glans and to prevent the penis foreskin from moving to the glans neck groove or over the plans; said longitudinal split has lipwise strengthened, opposing edges; and end portion of said second open end is shaped to taper curvingly towards the glans, an upper half of said second open end portion tapering towards the glans, and in which a wall surface limited by the mouth portion of the tubular shell element is anatomically shaped to correspond to and give support to the sloping rear surface of the glans, an edge of the wall of the tubular shell element limiting the open end being shaped and dimensioned to fit the deepening of the neck groove of the glans; wherein a lower half of said second open end divided by the longitudinal split tapers towards the glans, and in which there are outer tips of the tubular shell element, and in which bordering edges of the tubular shell element are shaped to leave the frenum of the penis free and to come into the deepening of the neck groove of the glans with the tips of the tubular shell element.

2. An impotence support according to claim 1 characterized in that the diameter of the mouth portion is fundamentally smaller in diameter than the diameter of the tubular shell element and is dimensioned to correspond to the thickness at the glans neck groove, when the diameter of the mouth portion is advantageously between 1.0 ... 1.8 cm and most advantageously about 1.3 cm.

3. An impotence support according to claim 1 characterized in that in the first open end of the tubular shell element is a flange like thickening.

4. A support for a penis comprising an open ended tubular shell element having a first open end and a second open end, said second open end shaped to taper down anatomically to fit into the deeper portion of the glans neck groove while leaving the penis frenum free, and preventing the foreskin from moving forward during intercourse, said second open end is formed with a mouth portion such that an edge bordering the mouth portion and edges bordering a split extending down said tubular shell element and an edge bordering the first open end have a common liplike thickening.

5. A support for a penis comprising an open ended tubular shell element having a first open end and a second open end, said second open end shaped to taper down anatomically to fit into the deeper portion of the glans neck groove while leaving the penis frenum free, and preventing the foreskin from moving forward during intercourse, said second open end is formed with a mouth portion such that in order to restrict and compress the mouth portion of the tubular shell element firmly into the glans neck groove to remain fundamentally the size of the neck groove during sexual intercourse, a binding element is intended to be stretched bridgewise across a split extending down said tubular shell element, such binding being advantageously adhesive plaster or some corresponding tape element, which is fastened to the tubular shell element outer surface.

6. A penis support for enabling sexual intercourse to be performed by a sufferer of impotency, comprising a tubular shell element having a first open end for facing the root of the penis and a second open end for facing the top of the penis, and a longitudinal split extending down said tubular shell element from said first open end to said second open end; wherein said second open end is formed with a mouth portion adapted to fit behind the penis glans and to prevent the penis foreskin from moving to the glans neck groove or over the glans; said longitudinal split has lipwise strengthened, opposing edges; an end portion of said second open end is shaped to taper curvingly towards the glans, an upper half of said second open end portion tapering towards the glans, and in which a wall surface limited by the mouth portion of the tubular shell element is anatomically shaped to correspond to and give support to the sloping rear surface of the glans, an edge of the wall of the tubular shell element limiting the open end being shaped and dimensioned to fit the deepening of the neck groove of the glans; wherein a lower half of said second open end divided by the longitudinal split tapers towards the glans, and in which there are outer tips of the tubular shell element, and in which bordering edges of the tubular shell element are shaped to leave the frenum of the penis free to come into the deepening of the neck groove of the glans with the tips of the tubular shell element, the diameter of the mouth portion is fundamentally smaller in diameter than the diameter of the tubular shell element and is dimensioned to correspond to the thickness at the glans neck groove, when the diameter of the mouth portion is advantageously between 1.0 ... 1.8 cm and most advantageously about 1.3 cm.

7. A penis support for enabling sexual intercourse to be performed by a sufferer of impotency, comprising a tubular shell element having a first open end for facing the root of the penis and a second open end for facing the top of the penis, and a longitudinal split extending down said tubular shell element from said first open end to said second open end; wherein said second open end is formed with a mouth portion adapted to fit behind the penis glans and to prevent the penis foreskin from moving to the glans neck groove or over the glans; said longitudinal split has lipwise strengthened, opposing edges; an end portion of said second open end is shaped to taper curvingly towards the glans, an upper half of said second open end portion tapering towards the glans, and in which a wall surface limited by the mouth portion of the tubular shell element is anatomically shaped to correspond to and give support to the sloping rear surface of the glans, an edge of the wall of the tubular shell element limiting the open end being shaped and dimensioned to fit the deepening of the neck groove of the glans; wherein a lower half of said second open end divided by the longitudinal split tapers towards the glans, and in which there are outer tips of the tubular shell element, and in which bordering edges of the tubular shell element are shaped to leave the frenum of the penis free and to come into the deepening of the neck groove of the glans with the tips of the tubular shell element, an edge bordering the mouth portion and edges bordering the split extending down said tubular shell element and an edge bordering the first open end have a common liplike thickening.

8. A penis support for enabling sexual intercourse to be performed by a sufferer of impotency, comprising a tubular shell element having a first open end for facing the root of the penis and a second open end for facing the top of the penis, and a longitudinal split extending down said tubular shell element from said first open end to said second open end; wherein said second open end is formed with a mouth portion adapted to fit behind the penis glans and to prevent the penis foreskin from moving to the glans neck groove or over the glans; said longitudinal split has lipwise strengthened, opposing edges; an end portion of said second open end is shaped to taper curvingly towards the glans, an upper half of said second open end portion tapering towards the glans, and in which a wall surface limited by the mouth portion of the tubular shell element is anatomically shaped to correspond to and give support to the sloping rear surface of the glans, an edge of the wall of the tubular shell element limiting the open end being shaped and dimensioned to fit the deepening of the neck groove of the glans; wherein a lower half of said second open end divided by the longitudinal split tapers towards the glans, and in which there are outer tips of the tubular shell element, and in which bordering edges of the tubular shell element are shaped to leave the frenum of the penis free and to come into the deepening of the neck groove of the glans with the tips of the tubular shell element, the first open end of the tubular shell element is a flange like thickening.

9. A penis support for enabling sexual intercourse to be performed by a sufferer of impotency, comprising a tubular shell element having a first open end for facing the root of the penis and a second open end for facing the top of the penis, and a longitudinal split extending down said tubular shell element from said first open end to said second open end; wherein said second open end is formed with a mouth portion adapted to fit behind the penis glans and to prevent the penis foreskin from moving to the glans neck groove or over the glans; said longitudinal split has lipwise strengthened, opposing edges; an end portion of said second open end is shaped to taper curvingly towards the glans, an upper half of said second open end portion tapering towards the glans, and in which a wall surface limited by the mouth portion of the tubular shell element is anatomically shaped to correspond to and give support to the sloping rear surface of the glans, an edge of the wall of the tubular shell element limiting the open end being shaped and dimensioned to fit the deepening of the neck groove of the glans; wherein a lower half of said second open end divided by the longitudinal split tapers towards the glans, and in which there are outer tips of the tubular shell element, and in which bordering edges of the tubular shell element are shaped to leave the frenum of the penis free and to come into the deepening of the neck groove of the glans with the tips of the tubular shell element, such that in order to restrict and compress the mouth portion of the tubular shell element firmly into the glans neck groove to remain fundamentally the size of the neck groove during sexual intercourse a binding element is intended to be stretched bridgewise across a split extending down said tubular shell element, such binding being advantageously adhesive plaster or some corresponding tape element, which is fastened to the tubular shell element outer surface.

10. An impotence support according to claim 5 or 9 characterized in that the retention of the first end and a central part of the tubular shell element around the penis is ensured with a further binding element advantageously plaster or corresponding tapes, which are stretched bridgewise over the split and fastened to the outer surface of the wall of the tubular shell element.

* * * * *

UNITED STATES PATENT AND TRADEMARK OFFICE
CERTIFICATE OF CORRECTION

PATENT NO. : 4,893,616

DATED : January 16, 1990

INVENTOR(S) : Toivo Immonen

It is certified that error appears in the above-identified patent and that said Letters Patent is hereby corrected as shown below:

Column 1 Line 32 "bo" should read --to--.

Column 3 Line 9 "an" should read --can--.

Column 3 Line 19 "its" should read --it--.(second occurrence)

Column 3 Line 29 "importance" should read --impotence--.

Column 4 Line 11 "an" should read --can--.

Column 4 Line 22 "If" should read --In--.

Column 4 Line 26 after "is" insert --a--.

Column 4 Line 46 "2" should read --22--.

Column 5 Line 25 "BOSTIK" should read --Bostik--.

Claim 1 Line 39 Column 5 "plans" should read --glans--.

Claim 6 Line 53 Column 6 after "free" insert --and--.

Signed and Sealed this

First Day of January, 1991

*Attest:*

HARRY F. MANBECK, JR.

*Attesting Officer*  *Commissioner of Patents and Trademarks*